United States Patent [19]

Schlein

[11] Patent Number: 4,855,064
[45] Date of Patent: Aug. 8, 1989

[54] APPARATUS AND METHOD FOR DECONTAMINATING VIRUS-INFECTED BODY FLUIDS

[75] Inventor: Allen P. Schlein, Fairfield County, Conn.

[73] Assignee: Viratec, Inc., Wilmington, Del.

[21] Appl. No.: 143,819

[22] Filed: Jan. 13, 1988

[51] Int. Cl.$^4$ .............................................. B01D 35/00
[52] U.S. Cl. .................... 210/764; 210/205; 210/206; 210/257.1; 210/258; 210/406; 604/4; 604/83; 604/317; 422/28; 422/37
[58] Field of Search ............... 210/696, 702, 749, 753, 210/744, 755, 756, 764, 808, 198.1, 205, 206, 209, 257.1, 258, 406, 416.1; 222/189, 372, 373, 145, 630; 422/28, 37; 604/317, 319, 322–326, 4, 83, 140, 147, 149, 269, 320, 321; 128/760

[56] References Cited

U.S. PATENT DOCUMENTS

| | | | |
|---|---|---|---|
| 3,520,300 | 7/1970 | Flower, Jr. | 604/269 |
| 3,552,568 | 1/1971 | Wade | 210/198.1 |
| 3,807,401 | 4/1974 | Riggle et al. | 604/269 |
| 3,887,468 | 6/1975 | Bray | 210/764 |
| 3,916,892 | 11/1975 | Latham, Jr. | 604/269 |
| 4,333,833 | 6/1982 | Longley et al. | 210/198.1 |
| 4,417,892 | 11/1983 | Meisch | 422/28 |
| 4,455,140 | 6/1984 | Joslin | 128/760 |
| 4,464,258 | 8/1984 | Wong et al. | 210/764 |
| 4,573,983 | 3/1986 | Annis | 210/205 |
| 4,584,106 | 4/1986 | Held | 210/206 |
| 4,617,117 | 10/1986 | Messinger et al. | 210/198.1 |
| 4,691,732 | 9/1987 | Johnson et al. | 210/198.1 |

Primary Examiner—W. Gary Jones
Attorney, Agent, or Firm—Spencer E. Olson

[57] ABSTRACT

A virus-infected body fluid is decontaminated as it is being collected, before it has had an opportunity to clot or thicken and before attending personnel are exposed to it, by introducing a suitable viricidal into the tubing through which the fluid is transported from the fluid source to a collection receptacle in an amount and concentration sufficient to substantially reduce the virus population in the collected fluid. In applications where suction is used to pull the fluid through the tubing, a venturi is used to draw a metered amount of liquid viricidal from a container into the tubing, and in cases when the fluid is transported by gravity, an in-line filter containing a suitable viricidal is connected in line with the tubing, the viricidal being leached from the filter by the fluid flowing through it. In both cases, the viricidal is thoroughly mixed with the fluid and continues to act on the collected fluid until its disposal.

6 Claims, 2 Drawing Sheets

APPARATUS AND METHOD FOR DECONTAMINATING VIRUS-INFECTED BODY FLUIDS

BACKGROUND OF THE INVENTION

This invention relates generally to the field of medicine, and more particularly to methods and apparatus for decontaminating virus-infected body fluids prior to their disposal.

Currently, one of the most widely discussed diseases, both in the medical profession and the public at large, is the feared AIDS epidemic and the problem of preventing its spread. While hospitals are taking precautions to prevent cross-infection between patients and particularly between AIDS patients and hospital personnel, for various reasons the precautions are not as effective as they might be. For example, under present State and Federal legislation and/or regulations physicians are not allowed to test a suspected AIDS patient without his or her permission because it is perceived as an invasion of privacy; as a countermeasure the Centers for Disease Control have advised physicians and hospitals to handle all patients as if they have AIDS, that is, impose a form of universal and total quarantine. This is an advisable course because even patients that might be willing to be tested are often brought into the hospital in emergency situations, thus exposing hospital personnel to potential risk of infection.

A serious problem in controlling the spread of the virus is the disposal of the biological waste of an AIDS patient. Just as in the case of nuclear waste disposal, only certain incinerators and dumps are approved for the disposal of biological waste. A site in Nevada has been approved as a national dump for nuclear materials, but to applicant's knowledge there is no national nor regional site for the dumping of biological waste. Currently, most of the biological waste collected in Connecticut medical facilities is transported by a Rhode Island contractor to a dump in Massachusetts; thus, it is necessary to store for some period of time contaminated body fluids such as blood and urine. The more prevalent current practice is to merely collect the waste body fluids and pour them down a drain completely untreated, relying on the belief that there is no cross-linkage in the hospital plumbing, that there is no ground seepage of these waste materials in areas that depend on septic systems for waste disposal and wells for water, or that the the virus will be killed by secondary chlorination in the city sewage system.

However, such reliance is not without serious risk; for example, some Connecticut cities and towns located along Long Island Sound close down their secondary chlorination plants during the winter months to save money and, furthermore, in some of the older cities the piping systems for secondary sewage are very old and their location generally unknown. In spite of this, in order to avoid the cost of shipping contaminated material to a remote location, the practice is to simply pour the contaminated waste material down the drain. Whichever course is followed, at some time hospital personnel have to handle and dump the contaminated body fluids, exposing them to risk, and the contaminated material, whether dumped down the drain or stored in an approved dump, presents a danger to the general population.

While it might appear that collected waste fluids could be decontaminated by simply adding a suitable viricidal to the collected fluid, this approach is unsatisfactory for two reasons: first, because to dump the viricidal into the collection receptacle would require active participation on the part of hospital or other personnel, there would always be a chance of spillage or splashing of the contaminated fluid with attendant risk of infecting such personnel; and secondly, if the fluid is held in the collection receptacle for any significant period of time, particularly if it is blood, it will tend to form large clots which limit the effectiveness of the viricidal in reaching and destroying virus that may be occluded by the clot.

Thus, it is clear that there is an urgent need for a solution to the problem of minimizing the risk of infection to both hospital personnel and the population at large due to the disposal of virus-infected waste body fluids. It is the primary object of the present invention to provide methods and apparatus for introducing a suitable viricidal into the waste body fluid before it has had much chance to clot or coagulate and in such a way that it will continue to act on the fluid after it is collected, so as to substantially reduce its virus population before any one has to handle the collection receptacle incident to disposal of its contents.

SUMMARY OF THE INVENTION

Briefly, the invention contemplates the introduction of a suitable viricidal into the waste body fluid as it is transported, usually through flexible tubing, from the fluid source to a collection receptacle, either by suction as is normally the case for blood, or by gravity in the case of urine, before the fluid has had an opportunity to clot o thicken. The viricidal, which may be any of a number of chemical disinfectants demonstrated as being effective for decontamination of the AIDS virus, is introduced in an amount and concentration sufficient to substantially reduce the virus population in the collected fluid. When suction is used to pull the fluid through the tubing, a venturi is used to draw a metered amount of viricidal, in liquid form, from a container into the tubing so as to be mixed with the body fluid as it is transported toward the collection receptacle. It may be desirable to add a small amount of an anti-coagulant and a small amount of surfacant to the viricidal to minimize clotting and to aid penetration of already clotted material by the viricidal, respectively. If the waste body fluid is transported through the tubing by gravity, say from a catheter to a urine collection bag, an in-line liquid filter containing a suitable viricidal, such as a chemical disinfectant, is connected in line with the tubing between the fluid source and the receptacle, the disinfectant being leached from the filter by the body fluid as it flows therethrough. In both cases, the viricidal becomes thoroughly mixed with the waste fluid as it is transported from the injection point to the collection receptacle and continues to act on the collected fluid until its disposal. Because the fluid is decontaminated at this stage, accidental spilling or splashing in the process of dumping it would not expose the person doing it to serious risk, and it can be dumped down the drain with minimal risk of the virus spreading to other hospital personnel or the general population.

The features of the invention considered to be novel are set forth in particular in the appended claims. The invention itself, however, both as to its construction and its method of operation, together with additional objects, features and advantages thereof, will be best understood from the following description of presently preferred embodiments when read in conjunction with the accompanying drawings.

DESCRIPTION OF PREFERRED EMBODIMENTS

Figure 1:
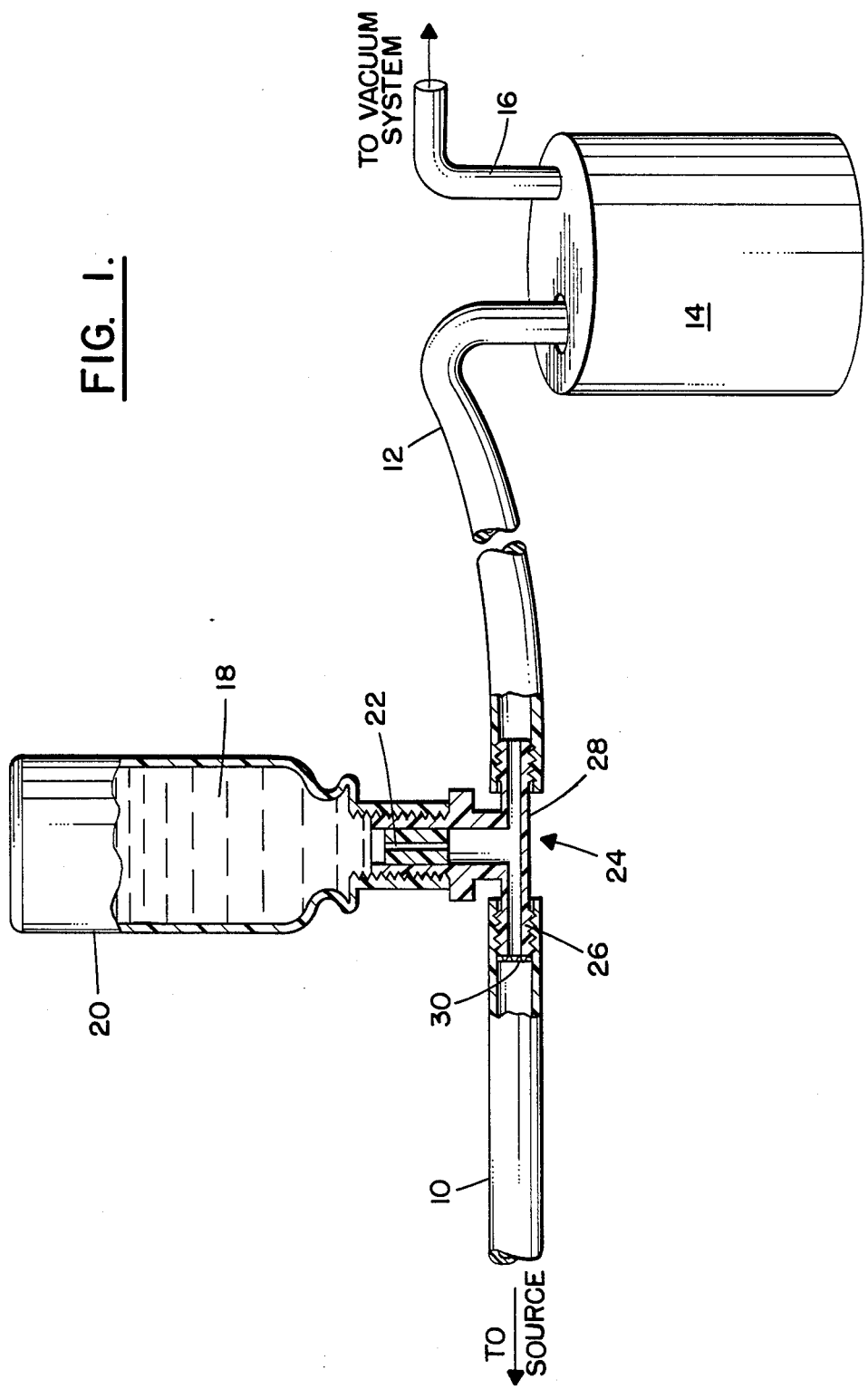
FIG. 1 is a schematic diagram of apparatus for decontaminating body fluid drawn by vacuum through a tubing connected between the fluid source and the collection receptacle.

The apparatus schematically illustrated in FIG. 1, intended for the decontamination of body fluids in situations where the fluid is drawn through a collection tube by suction, includes a first section 10 of flexible tubing, one end of which is connected to an aspirator, or the like, for introducing the body fluid into the tubing and a second section 12 of flexible tubing one end of which is vacuum sealed to a collection receptacle 14 of conventional design provided with a fitting 16 for connection to a vacuum pump (not shown). The illustrated collection vessel 14 is by way of example only and may take any of a variety of known forms of suction-type wound drainage systems such as bulbs, bellows, and the like. The system of FIG. 1 is intended for use primarily for the decontamination of virus-infected blood or other body fluid having a tendency to clot, and thus would have application in an operating room, a dental office or in a hospital emergency room or other areas where suction devices are commonly used for collection or disposal of waste blood.

In accordance with the invention, blood or other fluid transported through the tubing is decontaminated with a suitable viricidal, such as a liquid chemical disinfectant 18, which is drawn from a container 20, such as a small plastic bottle, into the tubing through a venturi 22 formed in the branch arm of a commercially available T-connector 24, the in-line arms 26 and 28 of which are coupled to tubing sections 10 and 12, respectively. The outer surfaces of arms 26 and 28 are barbed to enhance the connection of the tubing, and have a straight-through inner bore having a diameter of the order of $\frac{1}{8}$ to $\frac{1}{4}$ inch. The branch arm is externally threaded to threadably engage the internally threaded neck of the bottle 20. Liquid is drawn from the bottle 18 into the inner bore of arms 26 and 28 through a constricted passage 22, shown greatly exaggerated for clarity, typically having a diameter of 0.014 to 0.020 inch, by the reduced pressure in the tubing, much in the same way that fuel vapor is drawn from the carburetor bowl of an automobile. As the suction pulls the fluid, such as blood, through the tubing a metered amount of the liquid 18, determined by the relative diameters of the inner bore of the connector and the venturi 22, is drawn into the tubing where it is mixed with the body fluid as it flows toward the collection receptacle. A grid 30 is placed in tubing section 10, upstream from the connector, for mechanically breaking up any clots that may have formed.

The liquid 18 dispensed from the bottle 20 may be any of a number of commercially available chemical disinfectants which have been shown to be viricidal to the AIDS virus, including the nonionic detergents NP9 and NP40, sodium hypochlorite, alcohol and quaternary ammonium chloride, each with a concentration sufficiently high to largely destroy, at room temperature, any virus present in the collected fluid. It may be desirable to add an anti-coagulant, such as a small amount of Heparin, to the chemical disinfectant 18 to reduce clotting of the blood without, however, affecting its viricidal effect. A small amount of a surfactant may also be added to aid in penetration of the clotted material by the disinfectant.

If desired, instead of the T-connector 24 shown in FIG. 1, another commercially available form of T-connector designed for use with smaller-diameter tubing than that depicted in FIG. 1 and in which the tubing is secured to the in-line arms by threaded pressure fittings instead of barbs. The branch arm of this alternative form of connector is also externally threaded to receive the internally threaded neck of a bottle or other reservoir of liquid chemical detergent and is plugged except for a small opening, corresponding to the venturi 22 in FIG. 1, for metering the flow of detergent from the reservoir into the tubing.

It is also within the contemplation of the invention and preferable for cost and other reasons to replace the threaded connection of the container 20 to the branch arm 22 of the T-connector, be it of the type shown in FIG. 1 or the just-described alternative construction, with a press fit between the inner surface of the neck of the bottle and the outer surface of the branch arm; this construction permits the assembly of a bottle filled with a suitable viricidal to be pressed onto the branch arm of the connector and then sealed by heat, ultrasonically, or any other of the known methods for sealing two plastics parts together. By capping the ends of the in-line arms the filled bottle and the connector is marketable as an integral unit ready for connection by the user to sections of tubing of appropriate length for the particular application. Forming the reservoir for the disinfectant and the T-connector as an integral unit also prevents its re-use after the disinfectant has been dispensed.

Figure 2:
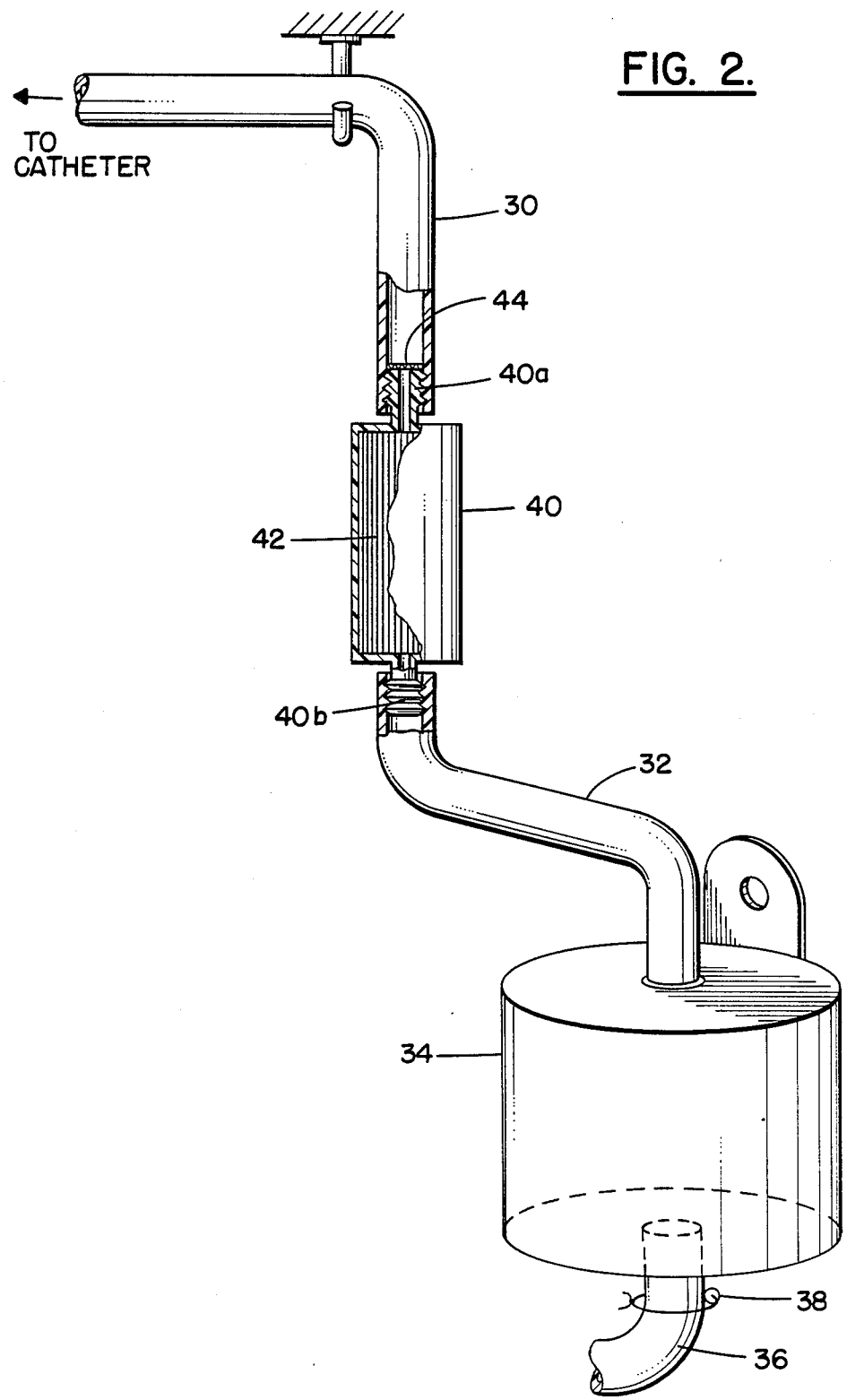
FIG. 2 is a schematic diagram of apparatus for decontaminating body fluids drawn by gravity from the source to the collection receptacle.

FIG. 2 schematically illustrates another embodiment of the invention which is useful in applications in which the waste body fluids are not as subject to clotting as blood and transportable by gravity through flexible tubing. More particularly, FIG. 2 depicts a urine collection system including a first section of flexible tubing 30 one end of which is connected to a catheter (not shown) or other device for introducing the fluid into the tubing, and a second section 32 of flexible tubing one end of which is connected and sealed to a urine collection bag 34 of conventional design provided with a discharge tube 36 through which the bag is emptied upon removal of a clamp 38. The other ends of tubing sections 30 and 32 are respectively connected to barbed connectors 40a and 40b, respectively, of an in-line filter 40 through which the fluid passes while being transported toward the collection bag. The filter 40 is of the type conventionally used in the gas line of internal combustion engines in that it consists of a cylinder, typically fabricated from a plastics material, which is sealed except for the connectors at either end and contains a filter element 42 consisting of accordion-folded paper to form a multiplicity of narrow longitudinal channels through which the liquid flows. In accordance with the present invention, before assembly in the casing the folded paper is impregnated with a suitable viricidal, such as one of the chemical disinfectants described above, with sufficient concentration that as the urine (or other similar body fluid) passes through the channels formed by the folded paper it will wet and leach off the viricidal in a concentration sufficient to substantially destroy the virus population in the collected fluid. Thus, the waste body fluid is simply transported by gravity through the in-line filter, which, in effect, functions as a miniature leaching field, to controllably introduce a viricidal into the fluid to be mixed therewith and to continue to act on it in the collecting bag. A grid 40 may be placed in the tubing, upstream from filter 40, for breaking up any clotting or thickening of the waste fluid.

As an alternative to the folded paper impregnated with a chemical disinfectant, the in-line filter 40 may be filled with resin beads coated with, or granules containing a viricidal agent, such as one of the chemical disinfectants in the aforementioned group, or other material from which the chemical disinfectant may be leached off by waste fluid passing through the filter.

Although preferred embodiments of apparatus for introducing a chemical disinfectant into waste body fluid as it is being collected to decontaminate such virus as it may contain, it will be evident to ones skilled in the art that the described methods can be implemented differently without departing from the spirit and scope of the invention as set forth in the following claims. For example, the aforementioned list of proven chemical disinfectants should not be construed as being exhaustive, the intention being to cover other known viricidal agents as well as those not yet developed shown to be effective in destroying the contaminating virus.

I claim:

1. A body fluid collection system for decontaminating a virus-infected body fluid as it is being transported from a source of the body fluid to a collection receptacle, said system comprising in combination:
   a collection receptacle for receiving and storing a fluid, said receptacle having a first port means for connection to a source of suction and a second port means for admitting a fluid into the receptacle;
   a section of tubing connected at one end to the second port of said collection receptacle and the other end comprising a means for connection to a source of body fluid and for transporting body fluid by suction from the source to said collection receptacle; and
   viricidal dispensing means connected in-line with said tubing between the source and the collection receptacle for introducing a viricidal agent into body fluid transported by suction through the tubing toward the collection receptacle, said dispensing means including a container having a constricted closure and containing a liquid viricidal agent with a predetermined concentration, and aspirating means comprising a T-shaped body having a bore extending through in-line arms each connected to one end of a respective segment of said tubing and a branch arm having an inlet to said bore and means for mounting said container with its constricted closure in communication with said bore, said aspirating means communicating suction pressure to said liquid viricidal agent in response to the flow of body fluid through said bore for causing a metered amount of viricidal agent to be sprayed from said container into the body fluid transported through said bore, said metered amount being sufficient to destroy the virus present in the fluid collected in said collection receptacle to a sufficient degree to permit safe disposal of the fluid.

2. Apparatus according to claim 1, wherein an anticoagulant is mixed with said viricidal agent for reducing clotting of said body fluid.

3. Apparatus according to claim 1, wherein a surfactant is mixed with said viricidal agent for aiding penetration by said viricidal agent into any clots present in the collected body fluid.

4. Apparatus according to claim 1, wherein said apparatus further comprises a grid placed in said tubing upstream from said T-connector for mechanically breaking up any clots present in the body fluid.

5. Apparatus according to claim 1, wherein said T-connector id formed of plastics material and said container is a bottle formed of plastics material joined to the branch arm of said T-connector.

6. Apparatus according to claim 5, wherein said container is a disposable bottle formed of plastics material integrally sealed to the branch arm of a disposable T-connector.

* * * * *